(12) United States Patent
Seefeldt

(10) Patent No.: US 11,779,880 B2
(45) Date of Patent: Oct. 10, 2023

(54) GAS SEPARATION SYSTEM AND GAS SEPARATION METHOD

(71) Applicant: 12M INVENT GMBH, Simmelsdorf (DE)

(72) Inventor: Kai Seefeldt, Pittenhart im Chiemgau (DE)

(73) Assignee: 12M INVENT GMBH, Simmelsdorf (DE)

( * ) Notice: Subject to any disclaimer, the term of this patent is extended or adjusted under 35 U.S.C. 154(b) by 155 days.

(21) Appl. No.: 17/496,827

(22) Filed: Oct. 8, 2021

(65) Prior Publication Data

US 2022/0111330 A1    Apr. 14, 2022

(30) Foreign Application Priority Data

Oct. 9, 2020   (EP) .................................... 20200977

(51) Int. Cl.
*B01D 53/22*   (2006.01)
*A61M 16/10*   (2006.01)
(Continued)

(52) U.S. Cl.
CPC ......... *B01D 53/226* (2013.01); *A61M 16/101* (2014.02); *A61M 16/105* (2013.01); *A61M 16/16* (2013.01); *A61M 16/20* (2013.01); *B01D 53/268* (2013.01); *B01D 65/00* (2013.01); *B01D 2053/223* (2013.01); *B01D 2256/12* (2013.01); *B01D 2256/22* (2013.01); *B01D 2257/102* (2013.01); *B01D 2311/04* (2013.01);
(Continued)

(58) Field of Classification Search
CPC .. A61M 16/16; A61M 16/105; A61M 16/101; A61M 16/20; B01D 2311/06; B01D 2317/025; B01D 2311/13; B01D 2257/102; B01D 2053/223; B01D 2311/04; B01D 2311/16; B01D 2317/08; B01D 2313/24; B01D 53/226; B01D 2256/22; B01D 2256/12; B01D 53/268; B01D 2311/246; B01D 2313/083; B01D 2311/25
See application file for complete search history.

(56) References Cited

U.S. PATENT DOCUMENTS 6,508,937 B1 * 1/2003 Kawashima ........... B01D 61/10
                                              210/636
7,044,158 B1 * 5/2006 Huff .................... F16K 37/0091
                                              210/779
(Continued)

FOREIGN PATENT DOCUMENTS

GB        2553790 A       3/2018
WO    2019141909 A1       7/2019

OTHER PUBLICATIONS

European Patent Office Extended Search Report for Application No. 20200977 dated Mar. 19, 2021 (2 pages).

*Primary Examiner* — Anthony R Shumate
(74) *Attorney, Agent, or Firm* — MICHAEL BEST & FRIEDRICH LLP

(57) ABSTRACT

A gas separation system for controlling a concentration of a first gas species and a second gas species in an outlet gas comprises a splitter unit. The splitter unit comprises a gas membrane system having a gas inlet port. The gas inlet port is in fluid connection with an air intake. A membrane is a selective barrier and allows some things to pass through but stops others.

14 Claims, 2 Drawing Sheets

$H_2O$   $H_2$   He   $CO_2$   $H_2S$   $O_2$            Ar   CO   $N_2$   $CH_4$

Fast ← — — Relative Permeation Rate — — → Slow

(51) Int. Cl.
  *A61M 16/16* (2006.01)
  *A61M 16/20* (2006.01)
  *B01D 53/26* (2006.01)
  *B01D 65/00* (2006.01)

(52) U.S. Cl.
  CPC ...... *B01D 2311/06* (2013.01); *B01D 2311/13* (2013.01); *B01D 2311/16* (2013.01); *B01D 2311/246* (2013.01); *B01D 2311/25* (2013.01); *B01D 2313/083* (2013.01); *B01D 2313/24* (2013.01); *B01D 2317/025* (2013.01); *B01D 2317/08* (2013.01)

(56) References Cited

U.S. PATENT DOCUMENTS

| | | | |
|---|---|---|---|
| 2012/0000355 A1 | 1/2012 | Sharma et al. | |
| 2013/0126430 A1* | 5/2013 | Kenley | B01D 61/00 210/638 |
| 2014/0231256 A1* | 8/2014 | Packingham | B01D 63/088 210/806 |
| 2014/0262989 A1* | 9/2014 | Pimentel | C02F 1/441 210/96.2 |
| 2015/0013434 A1* | 1/2015 | Hong | B01D 61/22 73/38 |
| 2015/0352403 A1 | 12/2015 | Ahmad | |
| 2016/0194222 A1* | 7/2016 | Volker | C02F 1/441 210/181 |
| 2017/0129795 A1* | 5/2017 | Singh | B01D 61/025 |
| 2020/0231465 A1* | 7/2020 | Zhang | B01D 61/22 |
| 2020/0297964 A1 | 9/2020 | Boulanger | |
| 2020/0398217 A1* | 12/2020 | Barraud | C10L 3/104 |
| 2021/0236986 A1* | 8/2021 | Thierry | C10L 3/104 |
| 2021/0268440 A1* | 9/2021 | Moon | B67D 1/00 |
| 2022/0098970 A1* | 3/2022 | Deshmukh | G01N 33/2823 |

\* cited by examiner

GAS SEPARATION SYSTEM AND GAS SEPARATION METHOD

BACKGROUND OF THE INVENTION

The invention relates to a gas separation system and a gas separation method for controlling a concentration of a first gas species, for example carbon dioxide CO2, and a second gas species, for example oxygen O2, in an outlet gas, the outlet gas for the use as breathing air.

In the field of providing breathing air to humans, it is known to enrich and/or deplete the oxygen content in air, which is being provided with the earth's atmosphere. As used herein, air is a gas mixture, which in a dry state consists of the main components nitrogen (N2) (78.08% by volume) and oxygen (O2) (20.95% by volume). In addition, there are noble gases (such as argon (Ar), helium (He), krypton and xenon) and other trace gases (such as carbon dioxide (CO2) (0.04% by volume), methane (CH4), hydrogen H2, nitrous oxide and carbon monoxide (CO)), which together make up less than 1% by volume. In addition to the above-mentioned gases, the air additionally contains water vapor, the content of which in the atmosphere varies over time and regionally and averages to 0.4% by volume.

Oxygen enriched breathing air may comprise more than 22% by volume of oxygen. For example, such a breathing air with reduced oxygen may relax a human.

According to an alternative application for providing breathing air with increased oxygen to humans, it is desirable to deplete the O2 under certain conditions in the breathing air. For example, such a breathing air with reduced oxygen may stimulate a hypoxia. Hypoxia is a condition in which the body or a region of the body is deprived of adequate oxygen supply at the tissue level. This may be useful to simulate, for example, high altitude trainings or simulate a stress situation. Oxygen depleted breathing air may comprise less than 20% by volume of oxygen. Preferably, the oxygen depleted breathing air may comprise less than 20% by volume of oxygen and more than 7% by volume of oxygen.

According to a further alternative, the concentration of other gas species in the breathing air may be enriched or depleted. For example, the concentration of CO2 or CO stimulates a human being, either by stressing the human or by relaxing the human.

For enriching or depletion of one gas species, such as O2 or CO2, the concentration of the at least one further component depends on the process used to enrich the oxygen content.

For example, to enrich the oxygen content, permeation systems may be used. In more detail, by permeating air through a membrane, oxygen concentration is adapted. In a typical membrane system, the incoming feed stream is separated into two components: permeant and retentate. Permeate is the gas that travels across the membrane and the retentate is what is left of the feed. The process of permeation involves the diffusion of molecules, called the permeate, through a membrane or interface. Permeation works through diffusion; the permeate will move from high concentration to low concentration across the membrane.

In more detail, the driving force for a gas to permeate through a membrane is the partial pressure difference; in other words, the partial gradient between the inside of the retentate side and the outside of the permeate side. The greater the difference, the more gas permeates through the membrane. For example, if oxygen and nitrogen are separated, as is the case of enriching breathing air with oxygen, a membrane effects that oxygen permeates through the membrane very quickly while the nitrogen tends to be held back.

A schematic of a permeation rate for a given membrane of some exemplary gas species is shown in FIG. 1. For example, O2 permeates faster through a given membrane than N2. Consequently, the permeate side can provide an O2 enriched breathing air. In this context is defined the permeability as a measure of the ability of a porous material (i.e. the membrane) to allow fluids, i.e. gas species, to pass through it. Herein is defined the permeability of a first gas species in relation to a second gas species. For example, as shown in FIG. 1, O2 has a higher permeability than N2. Further, CO2 has a higher permeability than O2.

Thus, by providing a constant feed stream and a pressure difference between retentate side and permeate side, preferably by feeding the membrane system with compressed air, the permeate has a higher concentration of O2, because it permeates more quickly, than the retentate, which comprises the held back N2. In other words, the feed stream has a lower concentration of the second gas species, e.g. O2, compared to the concentration of third gas species, e.g. N2. Due to the lower permeability of the third gas species N2, the second gas species O2 permeates through the membrane and the permeate is oxygen enriched.

A disadvantage of such a membrane system is that additionally a first gas component, e.g. CO2, is enriched in the permeate. In particular, in case of the first gas component being CO2, an increased concentration of the first gas component may malaise the human. At the expanse of the positive effect of enriching the breathing air with O2, which relaxes a human, the human is stressed by the increased amount of CO2.

It is known that a primary gas component, for example CO2, may be reduced for example by an absorbing material. For example, soda lime, which is a mixture of NaOH & Ca(OH)2 chemicals, can be used in granular form in gas separation systems, to remove CO2 from breathing gases to prevent CO2 retention and carbon dioxide poisoning.

A disadvantage of using a membrane system is that additionally a first gas component, e.g. CO2, is depleted in the retentate. In particular, in case of CO2, a depleted concentration of the first gas component may relax the human. At the expanse of the stress effect of depleting the breathing air with O2, which stresses a human, the human relaxes by the decreased amount of CO2.

It is known that the first gas component may be increased by adding the pure component. For example, in the case of a first gas component being CO2, pure CO2 is easily available.

SUMMARY OF THE INVENTION

In view of the above, the object of the invention is to provide a solution for controlling the amount of first gas species independently from a second gas species in breathing air, which is more simple in view of the known solutions for individually controlling CO2 and O2. In particular, an object is to reduce the amount of consumables such as an absorber material or providing a gas species from a gas bottle.

A further object is to avoid chemical reactions, e.g. caused by an absorber that changes by a chemical reaction the amount of the first gas species, in the gas separation system. Such a chemical reaction, however, may change in an undesirable way further gas species comprised in the output air.

A further object of the invention is to provide a gas control system which may provide both, an O2 enriched and O2 depleted breathing air and at the same time controlling the concentration individually of CO2 in the breathing air.

A further object of the invention is to provide a gas control system that can be operated with low maintenance efforts. For example, proving a gas control system that is not effected by pollution by condensed water and/or by exchanging consumables.

A further object of the invention is to provide a gas control system that allows for economically exploiting resources, for example reusing the outputs of the gas control system by feeding them at least partly back to the system rather than completely throwing them away.

A further object of the system is to provide a gas control system, which can be manufactured economically, for example, by reducing the number of different construction parts.

According to a first embodiment, a gas separation system for controlling a concentration of a first gas species and a second gas species in an outlet gas comprises a splitter unit. The splitter unit being a gas membrane system having a gas inlet port. The gas inlet port being in fluid connection with an air intake. A membrane is a selective barrier; it allows some things to pass through but stops others.

In more detail, at the gas inlet port a gas mixture is provided, i.e. feed in. The gas mixture contains at least the first gas species, preferably being CO2, the second gas species, preferably being O2, and a third gas species, preferably being N2. Advantageously, the input gas mixture is dry air, i.e. the concentration of water vapor is reduced compared to air provided by the atmosphere. Such dry air enables to reduce the pressure dew point thereby avoiding condensation of liquid water in the system.

Further, the splitter comprises a permeate outlet for outputting a permeate and a retentate outlet for outputting a retentate. In other words, the permeate outlet and the retentate outlet are separated by a membrane thereby enabling permeation by diffusion.

Diffusion is the net movement of anything (for example, atom, ions, molecules) from a region of higher concentration to a region of lower concentration. Diffusion is driven by a gradient in concentration. In particular, the pressure at the retentate side is higher than the pressure at the permeate side. By providing a given membrane the concentration of the first and the second gas species in the permeate is enriched compared to the concentration in the feed gas mixture.

Advantageously, a compressor is connected to the gas inlet port for increasing the pressure of the feed gas mixture. A compressor is a mechanical device that increases the pressure of a gas by reducing its volume. An air compressor is a specific type of gas compressor. Compressors are similar to pumps: both increase the pressure on a fluid and both can transport the fluid through a pipe. As gases are compressible, the compressor also reduces the volume of a gas. Alternatively or additionally, the pressure of the permeate may be reduced, for example, by a vacuum pump. Such configuration allows to control easily the pressure difference between permeate and retentate.

According to the first embodiment, the gas separation system further comprises a transfer unit having a membrane separating a retentate chamber from a permeate chamber, each chamber of the transfer unit having an output for outputting the outlet gas. Such a transfer unit enables a second stage gas separation.

Advantageously, the membrane of the transfer and the membrane of the splitter unit being made from the same material. Even more advantageously, the length and/or the thickens of the membranes being made of the same material may be different for the transfer unit and the separation unit.

Such a configuration allows similar diffusion properties of the membranes used in the transfer unit and the splitter unit. Further, using membranes from the same material reduces the part variety to construct the gas separation system.

Further, the retentate chamber for being fed with the permeate and the permeate chamber for being fed with the retentate. Such a configuration allows in the second gas separation step to vary the concentration of the first gas species relative to the second gas species in the outlet.

Further, the gas separation system according to the first embodiment comprises a directional control valve, which is fed with the retentate or the permeate. A directional control valves (DCVs) allows to control the fluid flow into different paths from the splitting unit. For example, the DCV being a switching element. The position of the switch permits flow being either 0% or 100% in one of the at least two output paths. Such a switching DCV is a particular economic solution for a DCV.

Advantageously, the gas separation system comprises two directional control valves, one which is fed with the retentate and one which is fed with the permeate.

Alternatively, the DCV being a gradually adjustment means. For example, the gradually adjustment means comprises of a flow manipulator, such as a spool inside a cylinder, which is mechanically or electrically actuated. The position of the gradually adjustment means restricts or permits flow, thus it controls the fluid flow from 0% to 100% in the at least two output paths.

Advantageously, the gas separation system further comprising a fluid control valve arranged between the retentate outlet or the permeate outlet and the directional control valve for controlling the flow rate of the retentate or the permeate, respectively. A control valve may be a switching means or a gradually adjustment means. For example, a switching means may be open or closed. Alternatively, a gradually adjustment means is a valve used to control fluid flow by varying the size of the flow passage as directed by a signal from a controller. This enables the direct control of flow rate and the consequential control of process quantities such as pressure, temperature, and liquid level. Such a configuration further enables to control the concentration of the first and the second gas species in the permeate compared to the concentration in the feed gas mixture.

According to the first embodiment, the gas separation system feeds a first part of the retentate to the permeate chamber of the transfer unit, the first part being transferred through the permeate chamber. In other words, the first part of the retentate is a sweep gas. A sweep gas is a gas present in the permeate side of a membrane reactor to change the partial pressure of the gas species and create a driving force. Here, the concentration of the first and the second gas species in the retentate is depleted compared to the concentration of the first and the second gas species in the permeate. Therefore, the partial pressure difference of the first and second gas species is increased. Further, the retentate chamber of the transfer unit is fed, for example by a direct gas connection or a second directional control valve, with the permeate.

Alternatively or additionally, the gas separation system feeds a first part of the permeate to the retentate chamber of the transfer unit, the first part being transferred through the retentate chamber. In other words, the driving force is changed by changing the composition in the retentate chamber. Further, the permeate chamber of the transfer unit is fed, for example by a direct gas connection or a second directional control valve, with the retentate. Additionally, the permeation rate given by the membrane of the transfer unit is different for the first gas species and the second gas species. Therefore, the partial pressure difference of the first and second gas species is different. Therefore, such a configuration allows to vary the concentration of the first gas species relative to the second gas species.

Further, the gas separation system mixes a second part of the retentate or permeate with the transferred first part at the output of the permeate chamber or retentate chamber, respectively, the second part being bypassed to the transfer unit. Further, the directional control wave is operable for controlling the flow rate of the transferred first part and the bypassed second part of the retentate or permeate. Bypassing a second part causes a pressure release of the transferred first part. Consequently, by controlling the bypassed amount of the second part, i.e. the bypassed amount being varied between 0% and 100%, the relative concentration of the first gas species to the second gas species can be controlled.

Advantageously, the permeation rate given by the membrane of the transfer unit is higher for the first gas species, preferably being $CO_2$ than for the second gas species, preferably being $O_2$. Such a configuration allows to use a membrane shown in FIG. 1 having a higher permeability for $CO_2$ than for $O_2$.

Even more advantageously, the concentration of the first gas species, preferably being $CO_2$, in the outlet gas of the permeate chamber is enriched compared to the concentration in the feed gas, preferably wherein the concentration of the first gas species, preferably being $CO_2$, by volume is enriched by a factor of up to two.

Such a configuration allows to provide breathing air that stresses a human, namely providing breathing air with reduced oxygen and at the same time having a concentration of $CO_2$ that is comparable to the concentration of $CO_2$ in dry air or even higher.

Additionally or alternatively, the concentration of the first gas species, preferably being $CO_2$, in the outlet gas of the retentate chamber is depleted compared to the concentration in the feed gas, preferably wherein the concentration by volume is depleted by a factor of up to two.

Such a configuration allows to provide breathing air that relaxes a human, namely providing breathing air with increased oxygen and at the same time having a concentration of $CO_2$ that is comparable to the concentration of $CO_2$ in dry air or even lower.

Advantageously, the permeation rate given by a membrane of the splitter unit is higher for the first and second gas species, preferably being $CO_2$ and $O_2$, respectively, compared to a permeation rate for the third gas species, preferably being $N_2$. Such a configuration allows to use a membrane shown in FIG. 1 having a higher permeability for $CO_2$ and $O_2$ than for $N_2$. The permeate may be further used to adapt the oxygen enriched/depleted air. Such a configuration further allows to use the same material for the membrane of the splitter unit and the transfer unit. For example, the length and/or the thickens of the membranes being made of the same material may be different for the transfer unit and the separation unit.

Even more advantageously, the concentration of the second gas species, preferably being $O_2$, in the permeate is enriched compared to the concentration in the feed gas, preferably wherein the concentration by volume is enriched by a factor of up to three. Such a configuration allows to provide a permeate that relaxes a human, namely providing a permeate with increased oxygen.

Additionally or alternatively, the concentration of the first gas species, preferably being $CO_2$, in the permeate is enriched compared to the concentration in the feed gas. Such a configuration allows to provide a sweep gas that can be used to increase the $CO_2$ in an outlet of the retentate chamber.

According to a further aspect, the gas separation system further comprises a humidifier. A humidifier is a device that changes concentration of water vapor in a gas.

In more detail, the humidifier has a second membrane separating a third chamber from a fourth chamber, wherein the third chamber is fed with an air gas mixture comprising the feed gas mixture and a fourth gas species, preferably being $H_2O$, and having an output connected to the gas inlet port, wherein the concentration of the fourth gas species in the output of the third chamber is depleted compared to the concentration in the ambient air gas mixture. Such a configuration allows to purify the gas mixture. For example, in the case the fourth gas species being $H_2O$ such a configuration allows avoiding condensation of water within the gas separator.

Additionally or alternatively, the fourth chamber is fed with the outlet gas, wherein the concentration of the fourth gas species, preferably being $H_2O$, in the output of the fourth chamber is enriched compared to the concentration in the outlet gas. Such a configuration allows to generate output gas more comparable to air as provided within the atmosphere. For example, in the case the fourth gas species being $H_2O$ such a configuration allows to increase breathability of the output gas. Such a configuration allows to purify the gas mixture. For example, in the case the fourth gas species being $H_2O$ such a configuration allows to provide dry air for the gas separator.

According to a further aspect, the gas separation system further comprises a water reducer having a third membrane separating a fifth chamber from a sixth chamber, the fifth chamber is fed with a compressed air gas mixture. In particular, the gas pressure in the fifth chamber is higher than in the gas pressure in the sixth chamber. For example, the gas pressure in the fifth chamber is increased by the compressor connected to the gas inlet port for increasing the pressure of the feed gas mixture. Further, the compressed air gas mixture comprises the feed gas mixture and a fourth gas species, preferably $H_2O$.

Further, the water reducer comprises a retentate outlet for outputting the feed gas mixture to the gas inlet port, wherein the concentration of fourth gas species, preferably being $H_2O$, in the feed gas mixture is depleted compared to the concentration of the fourth gas species in the compressed ambient air gas mixture. For example, in the case the fourth gas species being $H_2O$ such a configuration allows avoiding condensation of water within the gas separator. Such a configuration allows to purify the gas mixture. For example, in the case the fourth gas species being $H_2O$ such a configuration allows avoiding condensation of water within the gas separator. Additionally, such a configuration allows to more efficiently reduce the first gas species as the partial pressures are increased.

Even more advantageously, the gas separation system further comprises a second directional control valve, which is arranged between the water reducer and the gas inlet port, and feeds a part of the feed gas mixture to the sixth chamber. The concentration of the fourth gas species, preferably being $H_2O$, in the output of the sixth chamber is enriched compared to the concentration in the feed gas mixture. Further, the second directional control wave is operable for controlling the flow rate of the part of the feed gas mixture. Such a configuration allows to more efficiently reduce the fourth gas species as the partial pressures are increased. Additionally, such a configuration allows to more efficiently reduce the first gas species as the partial pressures are increased. The second DCV being operationally similar to the first DCV. Such a configuration allows reducing the parts variety.

Additionally or alternatively, the gas separation system further comprising a third directional control valve, which is fed with the outlet gas of the permeate chamber, and outputs a part of the outlet gas of the permeate chamber to an output port, wherein the third directional control wave is operable for controlling the flow rate of the part of the outlet gas of the permeate chamber.

Additionally or alternatively, the gas separation system further comprising a fourth directional control valve, which is fed with the outlet gas of the retentate chamber, and outputs a part of the outlet gas of the retentate chamber to an output port, wherein the fourth directional control wave is operable for controlling the flow rate of the part of the outlet gas of the retentate chamber.

The third and/or the fourth DCV being operationally similar to the first DCV. Such a configuration allows an additional and independent control of the first and second gas specifies provided to the output port.

Additionally, wherein an output of the third DCV and an output of the fourth DCVB are commonly connected to the output port.

According to a second embodiment, an air support system comprises a gas separation system in line with any aspect discussed above and a mask. In general, a mask provides mechanical means for feeding breathable air to the respiratory system of a human. In more detail, the mask may be adapted to cover mouth and nose of a human. Such a configuration allows more precisely controlling the flow path of the air provided to the human.

Alternatively, the output gas of the gas separation system may be fed to a sealed chamber. Such a configuration allows a human freely moving in the sealed chamber.

According to a further embodiment, a gas separation method for controlling a concentration of a first gas species, preferably being CO2, and a second gas species, preferably being O2, in an outlet gas, the outlet gas for the use as modified breathing air, comprises the steps of:
  providing a splitter unit for outputting a retentate and a permeate, wherein the concentration of the first and the second gas species in the retentate is depleted compared to the concentration of the first and the second gas species in a feed gas mixture, the feed gas containing at least the first gas species
  dividing, by a directional control valve, the retentate in a first part and a second part; feeding a first part of the retentate to the permeate chamber; controlling, by a control section, a flow rate of the first part of the retentate fed to the permeate chamber and the flow rate of a second part of the retentate so as to bypass the transfer unit;
  and/or
  dividing, by a directional control valve, the permeate in a first part and a second part; feeding a first part of the permeate to the retentate chamber; controlling, by a control section, a flow rate of the first part of the permeate fed to the retentate chamber and the flow rate of a second part of the permeate so as to bypass the transfer unit.

The invention will now be described in greater detail and in an exemplary manner using advantageous embodiments and with reference to the drawings. The described embodiments are only possible configurations in which, however, the individual features as described above can be provided independently of one another or can be omitted.

The accompanying drawings are incorporated into the specification and form a part of the specification to illustrate several embodiments of the present invention. These drawings, together with the description serve to explain the principles of the invention. The drawings are merely for the purpose of illustrating the preferred and alternative examples of how the invention can be made and used, and are not to be construed as limiting the invention to only the illustrated and described embodiments. Furthermore, several aspects of the embodiments may form—individually or in different combinations—solutions according to the present invention. The following described embodiments thus can be considered either alone or in an arbitrary combination thereof. The described embodiments are merely possible configurations and it must be borne in mind that the individual features as described above can be provided independently of one another or can be omitted altogether while implementing this invention. Further features and advantages will become apparent from the following more particular description of the various embodiments of the invention, as illustrated in the accompanying drawings, in which like references refer to like elements, and wherein:

BRIEF DESCRIPTION OF THE DRAWINGS

In the figures.

DETAILED DESCRIPTION

Figure 1:
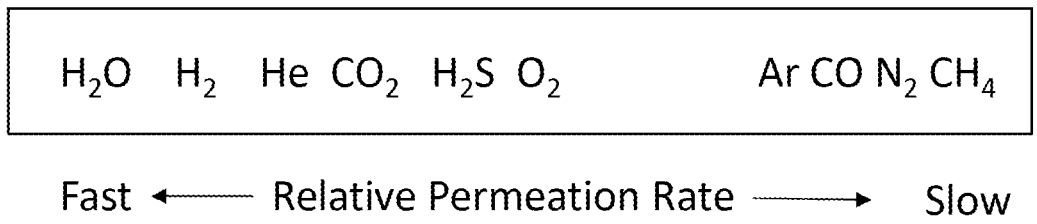
FIG. 1 is a schematic showing a relative permeation rate of various gas species.

The present invention will now be explained in more detail with reference to the Figures. Referring to FIG. 2, a schematic gas separation system 10 according to an embodiment is shown. The gas separation system 10 comprises a splitter unit 100, a transfer unit 200, and a directional control valve 300. Advantageously, the gas separation system further comprises at least one of a fluid control valve 400, a humidifier 500, a compressor 600, a water reducer 700, a second directional control valve 800, a third directional control wave 900, and/or a fourth direction control wave 950. These parts are all in fluid connection, for example by gas paths, which are indicated by solid or dashed lines in FIG. 1.

In more detail, splitter unit 100 has a gas inlet port 110, a permeate outlet 120, and a retentate outlet 130. The splitter unit 100 is operable, preferably by a not shown membrane, to separate gas species. The splitter unit 100 comprises a retentate chamber, which for example is separated by a membrane, from a permeate chamber. The retentate chamber is for example a tube with the gas inlet port 110 arranged at one end and the retentate outlet 130 at an opposing end. The permeate chamber surrounds the retentate chamber and has at least one permeate outlet. Advantageously, the relative permeation rates of the membrane of the splitter unit 100 are similar to those shown in FIG. 1. In particular, CO2 and O2 permeating faster through the membrane than N2. Such a configuration enables that a feed gas mixture containing at least O2, CO2, and N2 is separate in a permeate with enriched concentration of O2 and CO2.

The transfer unit 200 has a membrane separating a retentate chamber 220 from a permeate chamber 230. Advantageously, the relative permeation rates of the membrane of the transfer unit 200 are similar to those shown in FIG. 1. In particular, the permeation rate of CO2 is different to the permeation rate of O2.

In more detail, a tube with an inlet and an opposing output 222 for example forms the retentate chamber 220. The inlet of the retentate chamber 220 being in fluid connection with the permeate outlet 120 of the splitter unit 100, for example, by gas path. The permeate chamber 230 is for example formed by a ring tube. Such a ring tube surrounds the retentate chamber 220. The permeate chamber comprises an inlet and an output 232. The inlet of the permeate chamber 230 being in fluid connection with the retentate outlet 130 of the splitter unit, for example by a gas path.

The directional control valve 300 comprises an inlet and two outlets. The inlet is in fluid connection with the retentate outlet 130 of the splitter unit 100. A first outlet of the directional control valve 300 is in fluid connection with the inlet of the permeate chamber 230 of the transfer unit 200. The second outlet is in fluid connection with the output 232 of the permeate chamber 220 of the transfer unit 200. Such a configuration enables that a part or all of the retentate output from the splitter unit 100 is transferred through the permeate chamber 230. In other words, a part of the retentate is effective as a sweep gas that is effective in changing the partial pressure between the retentate chamber 220 and the permeate chamber 230. Additionally, the remaining part or all of the retentate is bypassed to the transfer unit 200. Such a configuration enables that the concentration of the first gas species is changed relative to the concentration of the second gas species.

According to an aspect, the gas separation system comprises the control valve 400, which is arranged in gas path between the retentate outlet 130 and the directional control valve 300. Such a configuration enables control of the concentration of the gas species in the permeate and the retentate output by the splitter unit. In particular, such a configuration enables pressure control.

According to a further aspect, the gas separation system comprises the humidifier 500, which has a second membrane separating a third chamber 510 from a fourth chamber 520. Advantageously, the humidifier 500 is additionally operable as a CO2 regulator. In other words, the membrane of the humidifier is not only selective for H2O but additionally selective for CO2. Consequently, the CO2 concentration output to gas section 9 is changed by the humidifier 500 to the CO2 concentration in the ambient air input at gas section 1. Such a configuration allows for reducing the membrane size of the splitter unit to separate O2 and N2.

Figure 2:
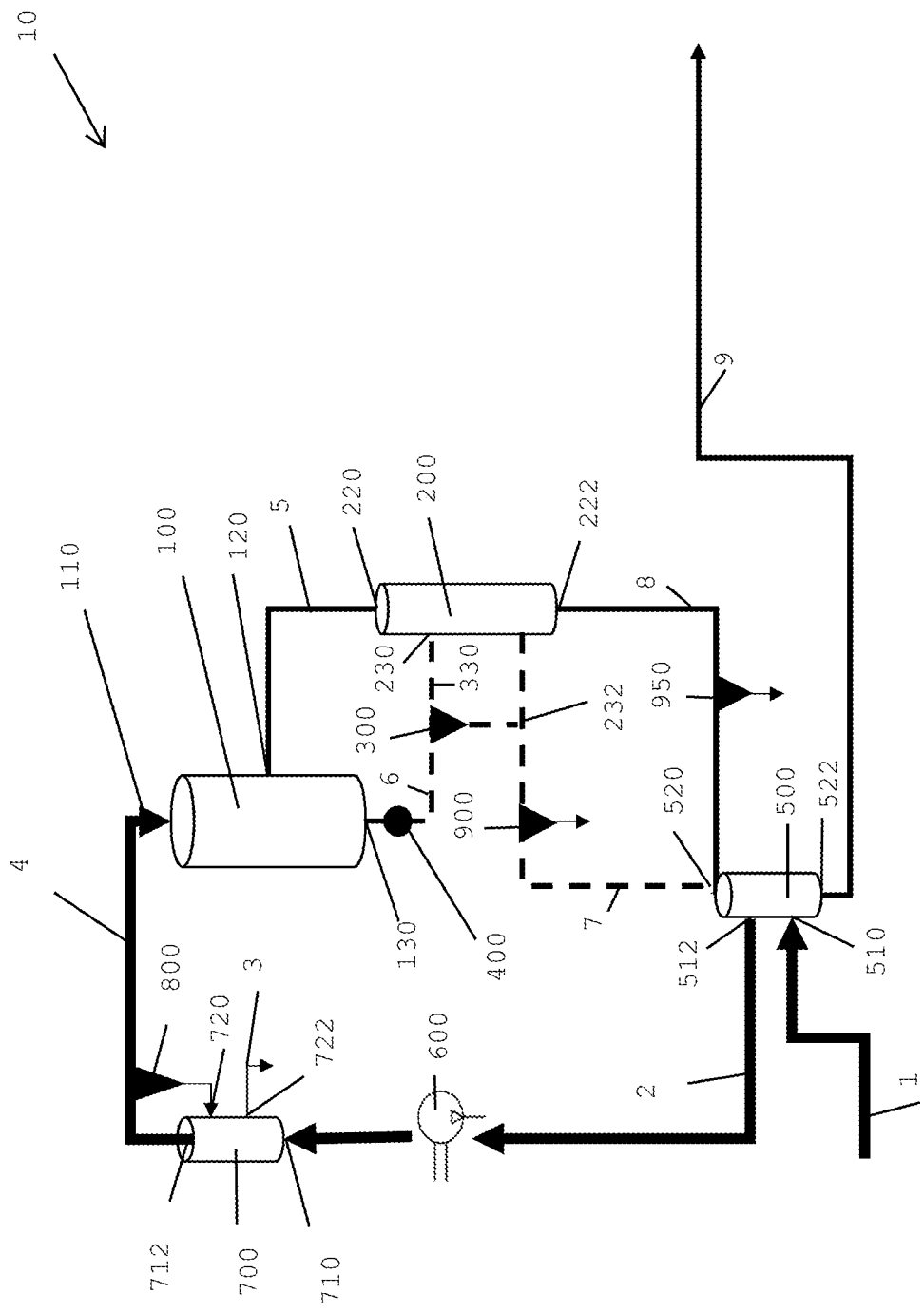
FIG. 2 is a schematic of a gas separation system according to an embodiment.

Even more advantageously, the relative permeation rates of the membrane of the humidifier are similar to those shown in FIG. 1. In particular, H2O permeates faster than O2, CO2, and N2. Such a configuration allows using one membrane material for the humidifier 500 and the splitter unit 100.

In more detail, the third chamber 510 is formed by a ring tube with an inlet and an opposing output 512. The output being in fluid connection with the gas inlet port 110. The inlet being fin connection to the air of the atmosphere for sucking air. Further, the fourth chamber 520 is for example formed by a tube that is surrounded by the third chamber 510. The inlet of the fourth chamber 520 being in fluid connection with the outlet of the transfer unit 200. For presentation purpose only two gas paths are shown, one from the retentate chamber of the transfer unit 200 and one from the permeate chamber of the transfer unit 200. Alternatively, one gas path may be provided from the transfer unit 200 and directional control valves may be provided to feed the output of the transfer unit to the one gas path. Such a humidifier 500 enables to reduce water vapor in the gas separation system and at the same time humidifies the output, which is the modified breathing air stressing or relaxing a human.

According to an aspect, the gas separation system further comprises a compressor 600, which has an output that is in fluid connected to the gas inlet port 110 and an inlet that is in fluid connection with the output 512 of the third chamber 510 of the humidifier. Such a configuration allows to increase the pressure of the feed gas mixture provided at the gas inlet port 110, thereby increasing the gas separation properties of the splitter unit.

According to a further aspect, the gas separation system further comprises the water reducer 700, which has a third membrane separating a fifth chamber 710 from a sixth chamber 720. Advantageously, the water reducer 700 is additionally operable as a CO2 reducer. In other words, the membrane of the water reducer 700 is not only selective for H2O but additionally selective for CO2. Consequently, the CO2 in the gas flows provided to the splitter unit 100 and the transfer unit 200 is reduced. Such a configuration allows for reducing the membrane size of the splitter unit to separate O2 and N2.

According to a further aspect, a permeation rate of the membrane of the splitter unit is adapted for providing a volume flow rate of the permeate that is less than the volume flow rate of the retentate. The volumetric flow rate (also known as volume flow rate, rate of fluid flow, or volume velocity) is the volume of fluid which passes per unit time. In more detail, in the application case of providing breathable air to a human the absolute amount of O2 needs to be constant for the human. In other words, the retentate having a depleted concentration of O2 needs to be provided with a higher volume flow rate than the O2 enriched permeate. Such a permeation rate of the membrane enables reducing the membrane size of the splitter unit.

Even more advantageously, the relative permeation rates of the membrane of the water reducer are similar to those shown in FIG. 1. In particular, H2O permeates faster than O2, CO2, and N2. Such a configuration allows using one membrane material for the water reducer 700 and the splitter unit 100. In more detail, the fifth chamber 710 is formed by a tube with an inlet and an opposing output 712. The output being in fluid connection with the gas inlet port 110. The inlet being in fluid connection with the output of the compressor. Further, the sixth chamber 720 is, for example, formed by a ring tube that surrounds the fifth chamber 710. The inlet of the sixth chamber 720 being in fluid connection with the outlet of the fifth chamber 710. Such a water reducer 700 enables to reduce water vapor in the gas separation system. The gas output from the sixth chamber 722 may be used for cooling the gas separation system.

According to a further aspect, the gas separation system further comprises the second directional control valve 800, which comprises an inlet and two outlets. The inlet being in fluid connection with the output 712 of the fifth chamber 710 of the water reducer. A first outlet being in fluid connection with the gas inlet port 110. The second outlet being in fluid connection with the input of the sixth chamber 720 of the water reducer 700. Such a configuration enables that a part of the dry gas output from the water reducer 700 is transferred through the sixth chamber 720. In other words, a part of the dry gas is effective as a sweep gas that is effective in changing the partial pressure between the fifth chamber 710 and the sixth chamber 720. Such a configuration enables that the feed gas mixture feed to the gas inlet port 110 is even more efficiently purified by reducing a gas species that permeates fast through the third membrane, for example H2O.

According to a further aspect, the gas separation system further comprises the third directional control valve 900, which comprises an inlet and two outlets. The inlet being in fluid connection with the output 232 of the permeate chamber 230. For presentation purpose, the output 232 is arranged in a T-shape part of the gas line connecting the outlets of the first directional control valve 300. A first outlet of the third directional control valve 900 being in fluid connection with the inlet of the fourth chamber 520 of the humidifier. The second outlet being in fluid connection with the atmosphere. Such a configuration enables that a flow rate of the gas output, which is used as modified breathing air, is adapted to the use of a human, which for example is being provided with a mask. The air output to the atmosphere may be further used for cooling the gas separation system.

Similarly, according to a further aspect, the fourth directional control valve 950 comprises an inlet and two outlets. The inlet being in fluid connection with the output 222 of the retentate chamber 230. A first outlet of the fourth directional control valve 950 being in fluid connection with the inlet of the fourth chamber 520 of the humidifier. The second outlet being in fluid connection with the atmosphere. Such a configuration enables that a flow rate of the gas output, which is used as modified breathing air, is adapted to the use of a human being provided with a mask. The air output to the atmosphere may be further used for cooling the gas separation system.

The above described gas separation system allows to control the concentration of CO2 independently from the concentration of O2 in a gas separator using membranes. Further, the use of membrane separators allows to protect the system from corrosion.

Further, in the following is described by way of example the composition of the gas mixture as changed by the gas separation system as described with reference to FIG. 2.

At the input gas section 1, air is provided at a temperature range between −20° C. to 100° C., preferably between 0° C. to 50° C., even more preferably between 18° C. and 38° C. The gas separation system operates independently from the relative humidity of the air. The pressure of the air is atmospheric pressure. The input flow is 47 l/min. The concentration of oxygen is approximately 21%. The concentration of CO2 is 0-10.000 ppm, preferably 1-3.000 ppm, and even more preferably between 1-1.500 ppm. Such a system enables that air can be provided that is not preprocessed.

At gas section 2, a gas mixture is provided to compressor 600, wherein the water concentration is reduced compared to the air provided at input gas section 1. Such a gas mixture reduces corrosion in the system.

At gas section 3, a gas mixture is thrown away or used for cooling of the gas separation system that has, for example a concentration of H2O of up to 99%. At the same time. the concentration of CO2 and O2 are increased proportional. For example, the concentration of CO2 is 1.000 ppm. The concentration of O2 is for example up to 28%. The high concentration of O2 is disadvantageous. However, this compromise is undertaken to avoid water in the gas separation system. Such a gas mixture provides cooling to the system.

At gas section 4, a gas mixture is provided to the splitter unit 100 having a concentration of CO2 of approximately 380 ppm which is dry. Such a gas mixture reduces corrosion in the system.

At gas section 5, a gas mixture is provided to the retentate chamber 220 at a lower flow rate than the input flow rate, preferably a third to half the input flow rate, for example of 17 l/min. For example, the O2 concentration is 34%. Preferably, the concentration of O2 is between 22% and 100%, even more preferably between 22 and 50%, even more preferably between 22 and 40%. The relative humidity is for example 80%, which is a not desired high concentration of humidity. Additionally or alternatively, concentration of CO2 is for example 1000 ppm, which is a not desired high concentration of CO2. Preferably the concentration of CO2 is higher than at gas section 1, for example higher than at gas section 1 and lower than four times of at gas section 1, even more preferably higher than at gas section 1 and lower than two times of at gas section 1. Such a gas mixture may be used to relax a human.

At gas section 6, a gas mixture is provided to the permeate chamber 230 at a lower flow rate than the input flow rate, preferably a third to half the input flow rate, for example of 24 l/min. The concentration of CO2 is for example 150 ppm, which is a not desired low concentration of CO2 and which is very dry. The relative humidity is for example 10%, Such a gas mixture, which is additionally reduced in the concentration of O2, may be used to stress a human.

In other words, at gas section 5 a gas is provided that is enriched with a first set of gas components permeating fast through the membrane (e.g., enriched with H2O, CO2, and O2) compared to a second set of gas components permeating slow through the membrane (e.g. N2). Similarly, at gas section 6 a gas is provided that is depleted with the first set of gas components permeating fast through the membrane (e.g., enriched with H2O, CO2, and O2) compared to the second set of gas components permeating slow through the membrane (e.g. N2).

At gas section 7, the same gas mixture is provided as at gas section 6 or the concentration of CO2 is enriched compared to the concentration at gas section 6. For example, the concentration of CO2 at gas section 6 being 150 ppm and at gas section 7 being 470 ppm comparable to the ambient air. The relative humidity at gas section 7 may be for example 30%. Such a gas mixture may be used to even more stress a human by enriching CO2.

At gas section 8, the same gas mixture is provided as at gas section 5 or the concentration of CO2 is depleted compared to the concentration at gas section 5. For example, the concentration of CO2 being 430 ppm instead of 1000 ppm. The relative humidity may be for example 30% Instead of 80%. Such a gas mixture may be used to even more relay a human by depleting CO2.

At gas section 9, the humidity of the gas mixture provided at gas section 7 or 8 may be increase to for example 57% so as to provide a humidity of ambient air. Such a gas mixture is nice to breath.

According to a further aspect, the gas system may comprise a sensor may be for measuring at least one of the concentration of the first and second gas species. Such a sensor allows to operate the gas system as a control loop. Advantageously, the sensor is arranged within gas section 9, in other words arranged in a gas section comprising the output port. Consequently, only one sensor is required for providing a control loop According to a further aspect, the gas system may comprise a processing unit for receiving sensor data from the sensor and for outputting control values for controlling at least one of the directional control valves and/or the control wave.

Even if not described with reference to the Figures, the gas separation system may be use to enrich or deplete one gas species compared to another gas species which have a similar relative permeation rate compared to a third gas species, which has a different relative permeation rate.

Even if not shown to the Figures, the output gas mixture may be feed to a mask or a sealed chamber.

Even not mentioned so far, a material for the membrane can be semipermeable. Only molecules or ions with certain properties will be able to diffuse across such a membrane. Permeation can occur through most materials including metals, ceramics and polymers. However, the permeability of metals is much lower than that of ceramics and polymers due to their crystal structure and porosity.

Alternatively or additionally to the compressor 600 a vacuum pump may be provided to the gas separation system.

Advantageously, at least a part of the membranes of the splitter unit 100, the transfer unit 200, the humidifier 500 and the water reducer 700 may be made of the same material.

Even if not discussed with the reference to the Figures, at gas section 1 not necessarily ambient air must be provided. For example, preprocessed air may be provided.

Even if in the above description the gas separation units, namely the splitter unit, the transfer units, the humidifier, and the water reducer, have been described with a tubular geometry, at least one may have a rectangular geometry comprising layered chambers.

The above description has to be understood that the directional control valve and the control wave may be either a switching element or a gradually adjustment means.

Alternatively to water, the water reducer and/or the humidifier may purify and/or enrich the feed gas and the output gas from a different gas species, for example CO2.

According to an embodiment not shown by the figures, the directional control valve may be arranged alternatively between the permeate outlet and the retentate chamber. In particular, the directional control valve comprises an inlet and two outlets. The inlet is in fluid connection with the permeate outlet of the splitter unit. A first outlet of the directional control valve is in fluid connection with the inlet of the retentate chamber of the transfer unit. The second outlet is in fluid connection with the output of the retentate chamber of the transfer unit. Such a configuration enables that a part or all of the permeate output from the splitter unit is transferred through the retentate chamber. In other words, a part of the permeate is effective in changing the partial pressure between the retentate chamber and the permeate chamber. Additionally, the remaining part or all the retentate is bypassed to the transfer unit. Such a configuration enables that the concentration of the first gas species is changed relative to the concentration of the second gas species.

According to an embodiment not shown by the figures, a second directional control valve may be arranged additionally between the permeate outlet and the retentate chamber.

The invention claimed is:

1. A gas separation system (10) for controlling a concentration of a first gas species and a second gas species in an outlet gas, the outlet gas for the use as breathing air, the gas separation system comprising:
    a splitter unit (100) having,
        a gas inlet port (110), which is fed with a feed gas mixture containing at least the first gas species, the second gas species, and a third gas species,
        a permeate outlet (120) for outputting a permeate, and
        a retentate outlet (130) for outputting a retentate,
            wherein the concentration of the first and the second gas species in the permeate is enriched compared to the concentration in the feed gas mixture;
    a transfer unit (200) having
        a membrane separating a retentate chamber (220) from a permeate chamber (230), each chamber of the transfer unit having an output (222, 232) for outputting the outlet gas,
    wherein the retentate chamber for being fed with the permeate and the permeate chamber for being fed with the retentate; and
    one of
        a directional control valve (300), which is fed with the retentate, for feeding a first part of the retentate to the permeate chamber (230) of the transfer unit (200), the first part for being transferred through the permeate chamber (230), and the direction control valve for mixing a second part of the retentate with the transferred first part at the output (232) of the permeate chamber, the second part for being bypassed to the transfer unit, wherein the directional control valve (300) is operable for controlling the flow rate of the transferred first part and the bypassed second part of the retentate; or
        a directional control valve (300), which is fed with the permeate, for feeding a first part of the permeate to the retentate chamber (220) of the transfer unit (200), the first part for being transferred through the retentate chamber (220), and the direction control valve for mixing a second part of the permeate with the transferred first part at the output (222) of the retentate chamber, the second part for being bypassed to the transfer unit, wherein the directional control valve (300) is operable for controlling the flow rate of the transferred first part and the bypassed second part of the permeate.

2. The gas separation system (10) according to claim 1, wherein a permeation rate given by the membrane of the transfer unit (200) is higher for the first gas species, preferably being CO2, than for the second gas species, preferably being O2.

3. The gas separation system (10) according to claim 2, wherein the concentration of the first gas species in the outlet gas of the permeate chamber (232) is enriched compared to the concentration in the feed gas, preferably wherein the concentration of the first gas species by volume is enriched by a factor of up to three.

4. The gas separation system (10) according to claim 2, wherein the concentration of the first gas species in the outlet gas of the retentate chamber (222) is depleted compared to the concentration in the feed gas, preferably wherein the concentration of the first gas species by volume is depleted by a factor of up to three.

5. The gas separation system (10) according to claim 1, wherein a permeation rate given by a membrane of the splitter unit is higher for the first gas species, preferably being CO2, and second gas species, preferably being O2, compared to a permeation rate for the third gas species, preferably being N2.

6. The gas separation system (10) according to claim 5, wherein the concentration of the second gas species in the permeate at the permeate outlet (120) is enriched compared to the concentration in the feed gas, preferably wherein the concentration of the second gas species by volume is enriched by a factor of up to three.

7. The gas separation system (10) according to claim 5, wherein the concentration of the first gas species in the permeate at the permeate outlet (120) is enriched compared to the concentration of the first gas species in the feed gas, preferably wherein the concentration by volume is enriched by a factor of up to four.

8. The gas separation system (10) according to claim 1, further comprising a fluid control valve (400) arranged between an outlet of the splitter unit and the directional control valve (300) for controlling the flow rate of the retentate.

9. The gas separation system (10) according to claim 1, further comprising a humidifier (500) having a second membrane separating a third chamber (510) from a fourth chamber (520),
 wherein the third chamber (510) is fed with an air gas mixture comprising the feed gas mixture and a fourth gas species, preferably being H2O, and having an output (512) connected to the gas inlet port (110), wherein the concentration of the fourth gas species in the output of the third chamber is depleted compared to the concentration in the air gas mixture and/or
 wherein the fourth chamber is fed with the outlet gas, wherein the concentration of the fourth gas species in an output (522) of the fourth chamber is enriched compared to the concentration in the outlet gas.

10. The gas separation system (10) according to claim 1, further comprising a compressor (600) connected to the gas inlet port (110) for increasing the pressure of the feed gas mixture.

11. The gas separation system (10) according to claim 1, further comprising
 a water reducer (700) having a third membrane separating a fifth chamber (710) from a sixth chamber (720), the fifth chamber is fed with a compressed air gas mixture, the compressed air gas mixture comprising the feed gas mixture and a fourth gas species, preferably H2O, and
 a retentate outlet (712) for outputting the feed gas mixture to the gas inlet port (110),
 wherein the concentration of fourth gas species in the feed gas mixture is depleted compared to the concentration of the fourth gas species in the compressed air gas mixture.

12. The gas separation system (10) according to claim 11, further comprising
 a second directional control valve (800), which is arranged between the water reducer (700) and the gas inlet port (110), and feeds a part of the feed gas mixture to the sixth chamber (720),
 wherein the concentration of the fourth gas species in an output (722) of the sixth chamber is enriched compared to the concentration in the feed gas mixture, and
 wherein the second directional control valve (800) is operable for controlling the flow rate of the part of the feed gas mixture.

13. The gas separation system according to claim 1, further comprising a third directional control valve (900), which is fed with the outlet gas of the permeate chamber, and outputs a part of the outlet gas of the permeate chamber to an output port, wherein the third directional control valve (900) is operable for controlling the flow rate of the part of the outlet gas of the permeate chamber, and/or further comprising a fourth directional control valve (950), which is fed with the outlet gas of the retentate chamber, and outputs a part of the outlet gas of the retentate chamber to an output port, wherein the fourth directional control valve (950) is operable for controlling the flow rate of the part of the outlet gas of the retentate chamber.

14. A system for feeding breathable air to a human, the system comprising a gas separation system (10) according to claim 1, further comprising a mask in fluid connection with the outlet gas.

* * * * *